US007923453B1

(12) United States Patent
Richards et al.

(10) Patent No.: US 7,923,453 B1
(45) Date of Patent: *Apr. 12, 2011

(54) METHODS OF CONVERTING A PATIENT'S TREATMENT REGIMEN FROM INTRAVENOUS ADMINISTRATION OF AN OPIOID TO ORAL CO-ADMINISTRATION OF MORPHINE AND OXYCODONE USING A DOSING ALGORITHM TO PROVIDE ANALGESIA

(75) Inventors: Patricia T. Richards, Bedminster, NJ (US); Warren C. Stern, Bedminster, NJ (US); Laurel J. Mengle-Gaw, St. Louis, MO (US); Benjamin D. Schwartz, St. Louis, MO (US)

(73) Assignee: QRxPharma Ltd., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/881,677

(22) Filed: Sep. 14, 2010

Related U.S. Application Data

(63) Continuation-in-part of application No. 12/579,173, filed on Oct. 14, 2009, now abandoned.

(51) Int. Cl.
*A01N 43/42* (2006.01)
*A01N 43/38* (2006.01)
*A01N 37/10* (2006.01)
*A61K 31/44* (2006.01)
*A61K 31/40* (2006.01)
*A61K 31/19* (2006.01)
*A61K 9/28* (2006.01)
*A61K 9/20* (2006.01)
*C07D 489/00* (2006.01)

(52) U.S. Cl. .......... 514/282; 546/44; 514/420; 514/568; 424/474; 424/468

(58) Field of Classification Search .............. 514/282, 514/420, 568; 546/44; 424/474, 468
See application file for complete search history.

(56) References Cited

U.S. PATENT DOCUMENTS

| 6,310,072 B1 | 10/2001 | Smith et al. |
| 2005/0053659 A1 | 3/2005 | Pace et al. |
| 2008/0039463 A1 | 2/2008 | Nadeson et al. |
| 2009/0291975 A1 | 11/2009 | Stern et al. |

FOREIGN PATENT DOCUMENTS

WO 2010/085848 8/2010

OTHER PUBLICATIONS

Kerri Wachter (Internal Medicine News, 2008).*
McPherson (Demystifying Opioid Conversion Calculations: A Guide for Effective Dosing, Publication date Aug. 25, 2009).*
Alberta Hospice document (Alberta Hospice Palliative Care Resource Manual 2001).*
Embeda® Prescribing Information, Jun. 2009.
Morphine Sulfate Prescribing Information, Mar. 2008.
Oxycontin® Prescribing Information, Apr. 16, 2010.
Opana® Prescribing Information, 2006.
Chevlen E., *J. Pain Symptom. Manag.*, 19:1 (2000) S42-9.
Ross et al., *Pain* 84 (2000) 421-28.
Riley et al., *Eur. J. Pain Suppl.*, 1 (2007) 23-30.
Riley et al., *Support Care Cancer* 14 (2006) 56-64.
Mercadante et al., *Cancer*, 95 (2002) 203-08.
Mercadante el al., *Cancer Treatment Reviews* 32 (2006) 304-15.
Mercadante, S., *Eur. J. Pain* 11 (2007) 823-30.
Holaday et al., *Perioperative Medizin*, 1:4 (2009) 244.
Kotlinska-Lemieszek , A., *J. Pain Symptom. Manag.*, 40:1 (2010) e10-e12.
Ladd et al., *Br. J. Clin. Pharmacol.*, 59:5 (2005) 524-35.
Grach et al., *Br. J. Clin. Pharmacol.*, 58:3 (2004) 235-42.
Smith et al., *Br. J. Clin. Pharmacol.*, 59:4 (2005) 486-87.
Anderson et al., *J. Pain Symptom Manage.*, 21:5 (2001) 397-406 ("Anderson").
Lichtor et al., *Anesth. Analg.*, 89 (1999) 732-38.
Foley, K., *N. Engl. J. Med.*, 313:2 (1985) 84-95.
Richards et al., *J. Pain* 10:4 (2009) S49; Richards et al., *Two Exploratory Double-Blinded Crossover Studies of the Treatment of Chronic Noncancer Pain: Efficacy and Safety of Concurrent Dosing of Morphine Plus Oxycodone vs Morphine Alone*, 2009 Annual Meeting of the America Pain Society, May 7-9, 2009, San Diego, CA.
Webster et al., *J. Pain* 11:4 (2010) S50.
Webster et al., *J. Pain* 11:4 (2010) S51.
Webster et al., *J. Pain* 11:4 (2010) S53.
Webster et al., *Single-Dose and Steady-State Pharmacokinetics of MaxDuo®, a Dual Opioid Formulation Containing a Fixed Ratio of Morphine and Oxycodone*, 29th Annual Meeting of the America Pain Society, May 6-8, 2010, Baltimore, MD.
www.palliative.org/PC/ClinicalInfo/AssessmentTools/MeanEquivalent%20for%20program%20v3.pdf, Jul. 26, 2010.
www.QRxPharma.com, Press Release, Sep. 1, 2010.
www.QRxPharma.com, Press Release, Aug. 17, 2010.
www.QRxPharrna.com, Press Release, May 4, 2010.
www.QRxPharma com, Press Release, Apr. 14, 2010.
www.QRxPharma.com, Press Release, Mar. 30, 2010.
www.QRxPharma.com, Press Release, Feb. 10, 2010.
www.QRxPharma.com, Press Release, Nov. 30, 2009.
www.QRxPharma.com, Press Release, Aug. 26, 2009.
www.QRxPharma.com, Press Release, Apr. 20, 2009.
www.QRxPharma.com, Press Release, May 22, 2008.
www.QRxPharma.com, Press Release, May 5, 2008.
Notification of Transmittal of the International Search Report and the Written Opinion of the International Searching Authority, or the Declaration, Patent Cooperation Treaty, Dec. 30, 2009, PCT/US09/62917.

* cited by examiner

*Primary Examiner* — Sreeni Padmanabhan
*Assistant Examiner* — Umamaheswari Ramachandran
(74) *Attorney, Agent, or Firm* — Frommer Lawrence & Haug LLP; Sandra Kuzmich; Russell A. Garman

(57) ABSTRACT

A method of converting a treatment for pain comprising intravenous administration of opioids, to a treatment for pain comprising oral administration of a first dose of an immediate release morphine-oxycodone combination in patients in need of analgesia. The method may comprise (1) determining a four-hour average oral morphine equivalents or determining a net average hourly intravenous dose, and (2) orally administering to the patient a first dose of a morphine-oxycodone combination in a 3:2 ratio by weight every four to six hours. Also, a method of treating pain in patients who had been administered opioids intravenously, comprising using a dosing algorithm to determine the first dose of the immediate release morphine-oxycodone combination.

20 Claims, No Drawings

METHODS OF CONVERTING A PATIENT'S TREATMENT REGIMEN FROM INTRAVENOUS ADMINISTRATION OF AN OPIOID TO ORAL CO-ADMINISTRATION OF MORPHINE AND OXYCODONE USING A DOSING ALGORITHM TO PROVIDE ANALGESIA

CROSS REFERENCE TO RELATED APPLICATION

This application is a continuation-in-part of U.S. patent application Ser. No. 12/579,173, filed on Oct. 14, 2009 now abandoned.

FIELD OF THE INVENTION

The present invention relates to treatment of pain in patients. In certain aspects, the present invention is directed to a method of converting a patient's pain treatment regimen from intravenous (IV) administration of an opioid to an orally administered combination of morphine and oxycodone in a weight ratio of about 3:2. This method may include the use of a dosing algorithm for determining an appropriate dosage of the morphine and oxycodone combination.

BACKGROUND OF THE INVENTION

Patients who experience significant pain as the result of, for example, a serious traumatic injury, a surgical procedure, or chronic illness (e.g., cancer), require relief through strong prescription medication. Opiate drugs are a class of pain-relieving prescription medications frequently used in the treatment of a variety of acute and chronic, moderate to severe, pain. Examples include natural opiates such as morphine, codeine, and thebaine; semi-synthetic opioids such as hydromorphone, hydrocodone, oxycodone, oxymorphone, diacetylmorphine (heroin), nicomorphine, dipropanoylmorphine, benzylmorphine, ethylmorphine, buprenorphine and morphine glucuronides (including the 3- and 6-glucuronide); and fully synthetic opioids such as alfentanil, fentanyl, remifentanil, sufentanil, trefentanil, pethidine, methadone, tramadol and dextropropoxyphene.

The World Health Organization's guidelines recommend that two strong opioids should not be co-administered, presumably because it is generally thought that all opioids exert their analgesic effects through the same receptor mechanisms in the central nervous system (CNS). See World Health Organization, Cancer Pain Relief and Palliative Care, Geneva: WHO 1990. Studies have shown, however, that the antinociceptive (also termed analgesic) effects of structurally related morphine and oxycodone are differentially antagonized by naloxonazine (a selective µ-opioid receptor antagonist) and nor-BN1 (a κ-selective opioid antagonist), respectively, indicating that they produce antinociception through different opioid receptor mechanisms. See Ross et al., *Pain* 1997, 73, 151-57. The opioid receptor is believed to have four receptor subtypes named µ-opioid receptor (MOR), σ-opioid receptor (SOR), κ-opioid receptor (KOR) and δ-opioid receptor (DOR). The biochemical and cellular effects of morphine are mediated through the MOR, found in high density within the CNS.

It has been found that co-administration to rats of sub-antinociceptive (also termed sub-analgesic) doses of morphine with sub-antinociceptive doses of oxycodone results in synergistic levels of antinociception. See Ross et al., *Pain* 2000, 84, 421-28. Animals that received the sub-antinociceptive doses of morphine with sub-antinociceptive doses of oxycodone were similar to placebo-injected control animals with respect to CNS side effects. See id at 424-25. Animals that received equipotent doses of either opioid alone were more sedated as compared to the control animals. See id at 425-26.

Synergistic analgesic effects of orally co-administering morphine and oxycodone at a 3:2 ratio have been demonstrated in patients (see, e.g., U.S. Pat. No. 6,310,072 and U.S. Publication Nos. 2005/0053659, 2007/0031489, 2009/0291975 and U.S. application Ser. No. 12/567,209). However, efficacy of treating pain by co-administering morphine and oxycodone is dependent, at least in part, on the quantity that is administered. For example, administration of a dosage of morphine and oxycodone will not produce analgesia if the quantity administered is too low. The quantity of morphine and oxycodone administered may also play a role in the occurrence of side effects that are common to opioids, such as nausea, vomiting, drowsiness, dizziness, mental clouding, dysphoria, pruritus, constipation, increased biliary tract pressure, urinary retention, hypotension, respiratory depression and bladder dysfunction. Moreover, the onset of tolerance to the therapeutic effects of the drugs, as well as the initiation of physical dependence, may occur with daily administration of opioids; the extent of such tolerance or physical dependence is dependent in part on the quantity of opioids administered. Therefore, it is important to determine an effective oral dosing regimen for co-administering morphine and oxycodone in order to effectively and safely treat pain.

The determination of the appropriate quantity of morphine and oxycodone to administer is especially important for patients recovering from a serious traumatic injury or a surgical procedure. These patients are often treated for pain initially by IV administration of an opioid drug such as morphine. Once these patients leave the hospital or surgical center and are no longer under medical supervision, they must receive the opioid drugs by a different route (e.g., orally) since repeated IV dosing is no longer practical. In the past, doctors have often estimated the necessary oral dose of some drugs following IV administration, but such practice often results in either over-medication, which can lead to adverse side effects, or under-medication, which can result in ineffective pain management. Also, physicians often consult equianalgesic tables before opioid rotation or conversion to determine a new safe starting dose appropriate for adequate pain control. Unfortunately, there are wide and clinically important differences in published opioid equianalgesic ratios. See Shaheen et al., *J. Pain Symptom. Manag.*, 38:3 (2009) 409-16. Thus, there is a need for a method of converting doses of intravenously administered opioids to an oral opioid dose that effectively manages the patient's pain and at the same time reduces or eliminates the problems associated with over- or under-medication. In particular, there is a need for a method of converting doses of intravenously administered opioid to orally co-administered morphine-oxycodone combination in a weight ratio of about 3:2

SUMMARY OF THE INVENTION

The present invention provides a method of treating pain in patients. In particular, the method addresses the need to convert the treatment regimen of patients who were receiving IV administration of an opioid in the hospital or surgical center, to oral doses of opioids, such as when IV dosing is no longer practical or appropriate to administer.

One aspect of the present invention is directed to a method of converting a treatment for pain comprising IV administration of an opioid to a treatment for pain comprising oral co-administration of an immediate release morphine-oxycodone combination (i.e., morphine, or a pharmaceutically acceptable salt thereof, and oxycodone, or a pharmaceutically acceptable salt thereof) in a weight ratio of about 3:2, in a human patient in need of analgesia, such that the method may comprise determining a four-hour average oral morphine equivalent dose of the opioid administered intravenously to the human patient, and orally co-administering to the human patient a first dose of an immediate release morphine-oxycodone combination in accordance to a dosing algorithm. Applying a dosing algorithm according to some embodiments of the invention, if the four-hour average oral morphine equivalent dose is between about 0 mg and about 30 mg, then the first dose of the morphine-oxycodone combination is no greater than about 12 mg of morphine, or a pharmaceutically acceptable salt thereof, and about 8 mg of oxycodone, or a pharmaceutically acceptable salt thereof. If the four-hour average oral morphine equivalent dose is greater than about 30 mg and less than or equal to about 40 mg, then the first dose of the morphine-oxycodone combination is about 18 mg of morphine, or a pharmaceutically acceptable salt thereof, and about 12 mg of oxycodone, or a pharmaceutically acceptable salt thereof. Further, if the four-hour average oral morphine equivalent dose is greater than about 40 mg and less than or equal to about 120 mg, then the first dose of the morphine-oxycodone combination is about 24 mg of morphine, or a pharmaceutically acceptable salt thereof, and about 16 mg of oxycodone, or a pharmaceutically acceptable salt thereof.

In some embodiments, if the four-hour average oral morphine equivalent dose is between about 0 mg and about 30 mg, then the first dose of the morphine-oxycodone combination is about 12 mg of morphine, or a pharmaceutically acceptable salt thereof, and about 8 mg of oxycodone, or a pharmaceutically acceptable salt thereof.

In certain embodiments, if the four-hour average oral morphine equivalent dose is between about 0 mg and about 10 mg, then the first dose of the morphine-oxycodone combination is about 3 mg of morphine, or a pharmaceutically acceptable salt thereof, and about 2 mg of oxycodone, or a pharmaceutically acceptable salt thereof. If the four-hour average oral morphine equivalent dose is greater than about 10 mg and less than or equal to about 15 mg, then the first dose of the morphine-oxycodone combination is about 6 mg of morphine, or a pharmaceutically acceptable salt thereof, and about 4 mg of oxycodone, or a pharmaceutically acceptable salt thereof. If the four-hour average oral morphine equivalent dose is greater than about 15 mg and less than or equal to about 20 mg, then the first dose of the morphine-oxycodone combination is about 9 mg of morphine, or a pharmaceutically acceptable salt thereof, and about 6 mg of oxycodone, or a pharmaceutically acceptable salt thereof. If the four-hour average oral morphine equivalent dose is greater than about 20 mg and less than or equal to about 30 mg, then the first dose of the morphine-oxycodone combination is about 12 mg of morphine, or a pharmaceutically acceptable salt thereof, and about 8 mg of oxycodone, or a pharmaceutically acceptable salt thereof.

Applying a dosing algorithm according to some embodiments of the invention, if the four-hour average oral morphine equivalent dose is between about 0 mg and about 30 mg, then the first dose of the morphine-oxycodone combination is about 12 mg of morphine, or a pharmaceutically acceptable salt thereof, and about 8 mg of oxycodone, or a pharmaceutically acceptable salt thereof. If the four-hour average oral morphine equivalent dose is greater than about 30 mg and less than or equal to about 40 mg, then the first dose of the morphine-oxycodone combination is about 18 mg of morphine, or a pharmaceutically acceptable salt thereof, and about 12 mg of oxycodone, or a pharmaceutically acceptable salt thereof. Further, if the four-hour average oral morphine equivalent dose is greater than about 40 mg and less than or equal to about 120 mg, then the first dose of the morphine-oxycodone combination is about 24 mg of morphine, or a pharmaceutically acceptable salt thereof, and about 16 mg of oxycodone, or a pharmaceutically acceptable salt thereof.

In some embodiments, the four-hour average oral morphine equivalent dose is determined by Equation (1):

$$\begin{pmatrix} \text{4-Hour Average} \\ \text{Oral Morphine} \\ \text{Equivalent Dose} \end{pmatrix} = \left(\frac{m-n}{h-4} \times 4\right) \times b \times s \qquad (1)$$

wherein m=total amount (mg) of oral morphine equivalents of the opioid used during IV administration (including bolus and PCA); n=oral morphine equivalents (mg) of the opioid used during the first four hours of IV administration; h=total time (hour) that the oral morphine equivalents of the opioid was administered intravenously; b=clinical bioequivalency factor; and s=safety factor.

In some embodiments, for the various opioids administered intravenously, the clinical bioequivalency factor is between about 1 and about 15. In other embodiments, the clinical bioequivalency factor is about 2. In some embodiments, the safety factor is between about 0.50 and about 1.0. In other embodiments, the safety factor is about 0.75.

Another aspect of the present invention is directed to a method of converting a treatment for pain comprising IV administration of morphine, or a pharmaceutically acceptable salt thereof, to a treatment for pain comprising oral co-administration of an immediate release morphine-oxycodone combination (i.e., morphine, or a pharmaceutically acceptable salt thereof, and oxycodone, or a pharmaceutically acceptable salt thereof) in a weight ratio of about 3:2, in a human patient in need of analgesia, such that the method may comprise determining a net average hourly IV morphine dose, and orally co-administering to the human patient a first dose of an immediate release morphine-oxycodone combination in accordance to an algorithm. Applying a dosing algorithm according to some embodiments of the invention, if the net average hourly IV morphine dose is between about 0 mg and about 9 mg, then the first dose of the morphine-oxycodone combination is no greater than about 12 mg of morphine, or a pharmaceutically acceptable salt thereof, and about 8 mg of oxycodone, or a pharmaceutically acceptable salt thereof. If the net average hourly IV morphine dose is greater than about 9 mg and less than or equal to about 14 mg, then the first dose of the morphine-oxycodone combination is about 18 mg of morphine, or a pharmaceutically acceptable salt thereof, and about 12 mg of oxycodone, or a pharmaceutically acceptable salt thereof. Finally, if the net average hourly IV morphine dose is greater than about 14 mg, then the first dose of the morphine-oxycodone combination is about 24 mg of morphine, or a pharmaceutically acceptable salt thereof, and about 16 mg of oxycodone, or a pharmaceutically acceptable salt thereof.

In some embodiments, if the net average hourly IV morphine dose is between about 0 mg and about 9 mg, then the first dose of the morphine-oxycodone combination is about 12 mg of morphine, or a pharmaceutically acceptable salt thereof, and about 8 mg of oxycodone, or a pharmaceutically acceptable salt thereof.

In some embodiments, if the net average hourly IV morphine dose is between about 0 mg and about 3 mg, then the first dose of the morphine-oxycodone combination is about 3 mg of morphine, or a pharmaceutically acceptable salt thereof, and about 2 mg of oxycodone, or a pharmaceutically acceptable salt thereof. If the net average hourly IV morphine dose is greater than about 3 mg and less than or equal to about 5 mg, then the first dose of the morphine-oxycodone combination is about 6 mg of morphine, or a pharmaceutically acceptable salt thereof, and about 4 mg of oxycodone, or a pharmaceutically acceptable salt thereof. If the net average hourly IV morphine dose is greater than about 5 mg and less than or equal to about 7 mg, then the first dose of the morphine-oxycodone combination is about 9 mg of morphine, or a pharmaceutically acceptable salt thereof, and about 6 mg of oxycodone, or a pharmaceutically acceptable salt thereof. If the net average hourly IV morphine dose is greater than about 7 mg and less than or equal to about 9 mg, then the first dose of the morphine-oxycodone combination is about 12 mg of morphine, or a pharmaceutically acceptable salt thereof, and about 8 mg of oxycodone, or a pharmaceutically acceptable salt thereof.

Applying a dosing algorithm according to certain embodiments of the present invention, if the net average hourly IV morphine dose is between about 0 mg and about 9 mg, then the first dose of the morphine-oxycodone combination is about 12 mg of morphine, or a pharmaceutically acceptable salt thereof, and about 8 mg of oxycodone, or a pharmaceutically acceptable salt thereof. If the net average hourly IV morphine dose is greater than about 9 mg and less than or equal to about 14 mg, then the first dose of the morphine-oxycodone combination is about 18 mg of morphine, or a pharmaceutically acceptable salt thereof, and about 12 mg of oxycodone, or a pharmaceutically acceptable salt thereof. If the net average hourly IV morphine dose is greater than about 14 mg, then the first dose of the morphine-oxycodone combination is about 24 mg of morphine, or a pharmaceutically acceptable salt thereof, and about 16 mg of oxycodone, or a pharmaceutically acceptable salt thereof.

In one aspect of the present invention, the net average hourly IV morphine dose may be determined by (i) calculating a net amount of morphine (or a pharmaceutically acceptable salt thereof) administered intravenously to the human patient, wherein the net amount is the total amount of morphine administered intravenously to the human patient minus the amount of morphine administered intravenously to the human patient during the first four hours of administration; (ii) calculating a net time that morphine was administered intravenously to the human patient, wherein the net time is the total time that morphine was administered intravenously minus four hours; and (iii) dividing the net amount of morphine administered intravenously to the human patient by the net time that morphine was administered intravenously to the human patient.

In certain embodiments, the pharmaceutically acceptable salt may be a hydrochloride, hydrobromide, hydroiodide, sulfate, bisulfate, nitrate, citrate, tartrate, bitartrate, phosphate, malate, maleate, napsylate, fumarate, succinate, acetate, terephthalate, pamoate or pectinate.

In particular embodiments, the morphine-oxycodone combination comprises morphine sulfate and oxycodone hydrochloride.

In some embodiments, the morphine-oxycodone combination may be in an immediate release dosage form, sustained release dosage form, or controlled release dosage form. In particular embodiments, the morphine-oxycodone combination may be in an immediate release dosage form.

In some embodiments, the morphine-oxycodone combination may be co-administered in a single dosage form. In other embodiments, the morphine-oxycodone combination may be co-administered in separate dosage forms.

In some embodiments, the IV opioid comprises morphine, codeine, thebaine, hydromorphone, hydrocodone, oxycodone, oxymorphone, diacetylmorphine (heroin), nicomorphine, dipropanoylmorphine, benzylmorphine, ethylmorphine, buprenorphine and morphine glucuronides (including the 3- and 6-glucuronide), alfentanil, fentanyl, remifentanil, sufentanil, trefentanil, pethidine, methadone, tramadol, dextropropoxyphene, a pharmaceutically acceptable salt thereof, or a combination thereof.

In certain embodiments, the IV opioid comprises morphine or oxycodone or a pharmaceutically acceptable salt thereof.

In certain embodiments, the method may further comprise orally co-administering one or more subsequent doses of morphine-oxycodone combination about every four to six hours, wherein the subsequent doses comprise the same amount of morphine, or a pharmaceutically acceptable salt thereof, and oxycodone, or a pharmaceutically acceptable salt thereof, as the first dose.

In various embodiments, if the patient has inadequate pain relief, then the method may further comprise orally co-administering one or more subsequent doses of morphine-oxycodone combination about every four to six hours, under the following conditions: if the first dose is about 3 mg of morphine, or a pharmaceutically acceptable salt thereof, and about 2 mg of oxycodone, or a pharmaceutically acceptable salt thereof, then the first subsequent dose is about 6 mg of morphine, or a pharmaceutically acceptable salt thereof, and about 4 mg of oxycodone, or a pharmaceutically acceptable salt thereof; if the first dose is about 6 mg of morphine, or a pharmaceutically acceptable salt thereof, and about 4 mg of oxycodone, or a pharmaceutically acceptable salt thereof, then the first subsequent dose is about 9 mg of morphine, or a pharmaceutically acceptable salt thereof, and about 6 mg of oxycodone, or a pharmaceutically acceptable salt thereof; if the first dose is about 9 mg of morphine, or a pharmaceutically acceptable salt thereof, and about 6 mg of oxycodone, or a pharmaceutically acceptable salt thereof, then the first subsequent dose is about 12 mg of morphine, or a pharmaceutically acceptable salt thereof, and about 8 mg of oxycodone, or a pharmaceutically acceptable salt thereof; if the first dose is about 12 mg of morphine, or a pharmaceutically acceptable salt thereof, and about 8 mg of oxycodone, or a pharmaceutically acceptable salt thereof, then the first subsequent dose is about 18 mg of morphine, or a pharmaceutically acceptable salt thereof, and about 12 mg of oxycodone, or a pharmaceutically acceptable salt thereof; and if the first dose is about 18 mg of morphine, or a pharmaceutically acceptable salt thereof, and about 12 mg of oxycodone, or a pharmaceutically acceptable salt thereof, then the first subsequent dose is about 24 mg of morphine, or a pharmaceutically acceptable salt thereof, and about 16 mg of oxycodone, or a pharmaceutically acceptable salt thereof.

In certain embodiments, if the patient experiences, for example, adverse effects with the first dose, then the method may further comprise orally co-administering one or more subsequent doses of morphine, or a pharmaceutically acceptable salt thereof, and oxycodone, or a pharmaceutically acceptable salt thereof about every four to six hours, under the following conditions: if the first dose is about 24 mg of morphine, or a pharmaceutically acceptable salt thereof, and about 16 mg of oxycodone, or a pharmaceutically acceptable salt thereof, then the first subsequent dose is about 18 mg of morphine, or a pharmaceutically acceptable salt thereof, and about 12 mg of oxycodone, or a pharmaceutically acceptable salt thereof; if the first dose is about 18 mg of morphine, or a pharmaceutically acceptable salt thereof, and about 12 mg of oxycodone, or a pharmaceutically acceptable salt thereof, then the first subsequent dose is about 12 mg of morphine, or a pharmaceutically acceptable salt thereof, and about 8 mg of oxycodone, or a pharmaceutically acceptable salt thereof; if the first dose is about 12 mg of morphine, or a pharmaceutically acceptable salt thereof, and about 8 mg of oxycodone, or a pharmaceutically acceptable salt thereof, then the first subsequent dose is about 9 mg of morphine, or a pharmaceutically acceptable salt thereof, and about 6 mg of oxycodone, or a pharmaceutically acceptable salt thereof; if the first dose is about 9 mg of morphine, or a pharmaceutically acceptable salt thereof, and about 6 mg of oxycodone, or a pharmaceutically acceptable salt thereof, then the first subsequent dose is about 6 mg of morphine, or a pharmaceutically acceptable salt thereof, and about 4 mg of oxycodone, or a pharmaceutically acceptable salt thereof; and if the first dose is about 6 mg of morphine, or a pharmaceutically acceptable salt thereof, and about 4 mg of oxycodone, or a pharmaceutically acceptable salt thereof, then the first subsequent dose is about 3 mg of morphine, or a pharmaceutically acceptable salt thereof, and about 2 mg of oxycodone, or a pharmaceutically acceptable salt thereof.

These and other objects, features and advantages of the present invention will become apparent after a review of the following detailed description.

DETAILED DESCRIPTION

The present invention relates to a method of converting a treatment for pain comprising IV administration of an opioid, to a treatment for pain comprising oral co-administration of a first dose of an immediate release morphine-oxycodone combination. The present invention also relates to a method of treating pain in patients who had been treated with IV administration of opioids, comprising converting the patients to a treatment comprising oral co-administration of a first dose of an immediate release morphine-oxycodone combination.

As used herein, "morphine" or "oxycodone" recited separately refers to the free base forms of morphine or oxycodone, respectively.

As used herein, "pharmaceutically acceptable salt" refers to a salt that is toxicologically safe for human and animal administration.

As used herein, "morphine-oxycodone combination" refers to a combination of morphine, or a pharmaceutically acceptable salt thereof, and oxycodone, or a pharmaceutically acceptable salt thereof.

As used herein, "morphine equivalent dose" refers to a calculation of the amount of morphine that produces the same analgesic effects as a particular amount of another opioid for given route(s) of dose administration. For example, the oral morphine equivalent dose of 1 mg of oral oxycodone is 1.5 mg of oral morphine; in other words, 1 mg of oxycodone administered orally will provide the same analgesic effect as 1.5 mg of morphine administered orally.

As used herein, "administration concurrently or co-administration" refers to the administration of a single composition containing both morphine and oxycodone, or pharmaceutically acceptable salts thereof, or to the administration of each opioid agonist as a separate composition within a short enough period of time such that the effective result is equivalent to that obtained when both such opioid agonists are administered as a single composition.

As used herein in the context of a number, or a range of numbers, "about" will be understood to embrace somewhat larger or smaller values than the indicated value to account for, as examples, experimental errors inherent in the measurement and variability between different methodologies for measuring the value, as will be apparent to one skilled in the art.

Methods of Converting Patients from IV Administration of Opioids

Embodiments of the present invention relate to a method of converting a treatment for pain comprising IV administration of an opioid to a treatment for pain comprising oral co-administration of a first dose of immediate release morphine and oxycodone, or pharmaceutically acceptable salts thereof, in patients in need of analgesia.

In certain embodiments, the IV administration of opioids may be by PCA. In some embodiments, the opioid administered intravenously may be any compound, such as a drug, that binds to opioid receptors. Examples of an opioid include, but are not limited to, morphine, oxycodone, codeine, hydrocodone, diamorphine, fentanyl, alfentanyl, buprenorphine, hydromorphone, methadone, and oxymorphone.

A dosing algorithm may be used to determine the first oral immediate release dose of the morphine-oxycodone combination. In some embodiments, a four-hour average oral morphine equivalent dose may be initially calculated based on the conditions of the IV administration of opioids, after which the first dose of the morphine-oxycodone combination is determined.

The four-hour average oral morphine equivalent dose may be determined using Equation $$\begin{pmatrix} \text{4-Hour Average} \\ \text{Oral Morphine} \\ \text{Equivalent Dose} \end{pmatrix} = \left( \frac{m-n}{h-4} \times 4 \right) \times b \times s \tag{1}$$

wherein m=total amount (mg) of oral morphine equivalents of the opioid used during IV administration (including bolus and PCA); n=oral morphine equivalents (mg) of the opioid used during the first four hours of IV administration; h=total time (hour) that the oral morphine equivalents of the opioid was administered under IV administration; b=clinical bioequivalency factor; and s=safety factor.

The term, "net amount of oral morphine equivalents administered," may be used to describe the oral morphine equivalents used during IV administration, minus the oral morphine equivalents used during first four hours of IV administration (m−n). The term, "net time administered," may be used to describe the total hours that the oral morphine equivalents was administered IV less four hours (h−4). "Net average hourly intravenous dosing" is therefore the net amount of oral morphine equivalents administered divided by the net time administered.

In Equation 1, the calculation of (m−n) and (h−4) essentially exempts from the ultimate determination the opioid given during the first four hours of intravenous administration. The first four hours are exempt because the amount of an opioid administered intravenously immediately following surgery or trauma is not generally indicative of analgesia required by the patient. During these initial hours the patient is likely under the influence of the analgesia used during surgery and/or would have little mobility that may not necessitate the need for a heightened level of analgesia that is often required throughout later stages of recovery.

A factor of four is used in Equation 1 to convert the net average hourly IV dosing ((m−n)/(h−4)) into a four-hour average since oral dosing of the morphine-oxycodone combination will be about every four to six hours.

The clinical bioequivalency factor considers the differences in the bioavailability between IV and oral routes of opioid administration and the conversion of non-morphine opioid analgesics to a morphine equivalent dose. In certain embodiments, the clinical bioequivalency factor for various opioids may vary between about 1 and about 15. The range also accounts for inter-patient variability, including the variability between opioid naïve and opioid tolerant patients. In some embodiments, the clinical bioequivalency factor for various opioids may vary between about 1 and about 10. For IV morphine, or a pharmaceutically acceptable salt thereof, the clinical bioequivalency factor may vary between about 1 and about 5. In certain embodiments, the clinical bioequivalency factor for morphine, or a pharmaceutically acceptable salt thereof, may be about 2. In some embodiments, the clinical bioequivalency factor for oxycodone, or a pharmaceutically acceptable salt thereof, may be between about 1.5 and 7.5. In other embodiments, the clinical bioequivalency factor for oxycodone, or a pharmaceutically acceptable salt thereof, may be between about 3 and about 5.

The safety factor allows for a lesser amount of oral morphine-oxycodone combination to be administered to minimize the chance of overdosing or occurrence of adverse events upon administration of the first dose. The safety factor may range from about 0.25 to about 1.0. In certain embodiments, the safety factor may be about 0.50. In some embodiments, the safety factor may be about 0.75.

In certain embodiments, when the four-hour average oral morphine equivalent dose may be known or calculated as described above, the first dose of an immediate release morphine-oxycodone combination can be determined using the dosing algorithm shown in Table 1.

TABLE 1

Algorithm for the Conversion of Four-Hour Average Oral Morphine Equivalents to a First Dose of an Immediate Release Morphine-Oxycodone Combination Administered Orally.

| Four-Hour Average Oral Morphine Equivalent Dose | First Dose of Morphine-Oxycodone Combination |
|---|---|
| 0-30 mg | No greater than 12 mg/8 mg |
| >30-≦40 mg | 18 mg/12 mg |
| >40-≦120 mg | 24 mg/16 mg |

According to the dosing algorithm of Table 1, if the four-hour average oral morphine equivalent dose is between about 0 mg and about 30 mg, the corresponding first dose of morphine-oxycodone combination may be no greater than about 12 mg/8 mg; if the four-hour average oral morphine equivalent dose is greater than about 30 mg and less than or equal to about 40 mg, the corresponding first dose of morphine-oxycodone combination may be about 18 mg/12 mg; if the four-hour average oral morphine equivalent dose is greater than about 40 mg and less than or equal to about 120 mg, the corresponding first dose of morphine-oxycodone combination may be about 24 mg/16 mg.

In some embodiments in which the four-hour average oral morphine equivalent dose is between about 0 mg and about 30 mg, the first dose of an immediate release morphine-oxycodone combination administered orally can be determined using the dosing algorithm shown in Table 2.

TABLE 2

Algorithm for the Conversion of Four-Hour Average Oral Morphine Equivalents to a First Dose of an Immediate Release Morphine-Oxycodone Combination Administered Orally.

| Four-Hour Average Oral Morphine Equivalent Dose | First Dose of Morphine-Oxycodone Combination |
|---|---|
| 0-10 mg | 3 mg/2 mg |
| >10-≦15 mg | 6 mg/4 mg |
| >15-≦20 mg | 9 mg/6 mg |
| >20-≦30 mg | 12 mg/8 mg |

According to the dosing algorithm of Table 2, if the four-hour average oral morphine equivalent dose is between about 0 mg and about 10 mg, the corresponding first dose of morphine-oxycodone combination may be about 3 mg/2 mg; if the four-hour average oral morphine equivalent dose is greater than about 10 mg and less than or equal to about 15 mg, the corresponding first dose of morphine-oxycodone combination may be about 6 mg/4 mg; if the four-hour average oral morphine equivalent dose is greater than about 15 mg and less than or equal to about 20 mg, the corresponding first dose of morphine-oxycodone combination may be about 9 mg/6 mg; if the four-hour average oral morphine equivalent dose is greater than about 20 mg and less than or equal to about 30 mg, the corresponding first dose of morphine-oxycodone combination may be about 12 mg/8 mg.

In some embodiments, when the four-hour average oral morphine equivalent dose may be known or calculated as described above, the first dose of an immediate release morphine-oxycodone combination administered orally can be also determined using the dosing algorithm shown in Table 3.

TABLE 3

Algorithm for the Conversion of Four-Hour Average Oral Morphine Equivalent Dose to a First Dose of an Immediate Release Morphine-Oxycodone Combination Administered Orally.

| Four-Hour Average Oral Morphine Equivalent Dose | First Dose of Morphine-Oxycodone Combination |
|---|---|
| 0-30 mg | 12 mg/8 mg |
| >30-≦40 mg | 18 mg/12 mg |
| >40-≦120 mg | 24 mg/16 mg |

According to the dosing algorithm of Table 3, if the four-hour average oral morphine equivalent dose is between about 0 mg and about 30 mg, the corresponding first dose of morphine-oxycodone combination may be about 12 mg/8 mg; if the four-hour average oral morphine equivalent dose is greater than about 30 mg and less than or equal to about 40 mg, the corresponding first dose of morphine-oxycodone combination may be about 18 mg/12 mg; if the four-hour average oral morphine equivalent dose is greater than about 40 mg and less than or equal to about 120 mg, the corresponding first dose of morphine-oxycodone combination may be about 24 mg/16 mg.

In certain embodiments, when the net average hourly intravenous dosing may be known or calculated as described above, the first dose of an immediate release morphine-oxycodone combination administered orally can be determined using the dosing algorithm shown in Table 4.

TABLE 4

Algorithm for the Conversion of Net Average Hourly Intravenous Dosing to a First Dose of an Immediate Release Morphine-Oxycodone Combination Administered Orally.

| Net Average Hourly Intravenous Dosing | First Dose of Morphine-Oxycodone Combination |
|---|---|
| 0-9 mg | No greater than 12 mg/8 mg |
| >9-≦14 mg | 18 mg/12 mg |
| >14 mg | 24 mg/16 mg |

According to the dosing algorithm of Table 4, if the net average hourly intravenous dosing is between about 0 mg and about 9 mg, the corresponding first dose of morphine-oxycodone combination may be no greater than about 12 mg/8 mg; if the net average hourly intravenous dosing is greater than about 9 mg and less than or equal to about 14 mg, the corresponding first dose of morphine-oxycodone combination may be about 18 mg/12 mg. If the net average hourly intravenous morphine administered is greater than about 14 mg, the corresponding first dose of morphine-oxycodone combination may be about 24 mg of morphine and about 16 mg of oxycodone.

In some embodiments in which the net average hourly intravenous dosing is between about 0 mg and about 9 mg, the first dose of an immediate release dose of a morphine-oxycodone combination administered orally can be determined using the dosing algorithm shown in Table 5.

TABLE 5

Algorithm for the Conversion of Net Average Hourly Intravenous Dosing to a First Dose of an Immediate Release Morphine-Oxycodone Combination Administered Orally.

| Net Average Hourly Intravenous Dosing | First Dose of Morphine-Oxycodone Combination |
|---|---|
| 0-3 mg | 3 mg/2 mg |
| >3-≦5 mg | 6 mg/4 mg |
| >5-≦7 mg | 9 mg/6 mg |
| >7-≦9 mg | 12 mg/8 mg |

According to the dosing algorithm of Table 5, if the net average hourly intravenous dosing is between about 0 mg and about 3 mg, the corresponding first dose of morphine-oxycodone combination may be about 3 mg/2 mg; if the net average hourly intravenous dosing is greater than about 3 mg and less than or equal to about 5 mg, the corresponding first dose of morphine-oxycodone combination may be about 6 mg/4 mg; if the net average hourly intravenous dosing is greater than about 5 mg and less than or equal to about 7 mg, the corresponding first dose of morphine-oxycodone combination may be about 9 mg/6 mg; if the net average hourly intravenous dosing is greater than about 7 mg and less than or equal to about 9 mg, the corresponding first dose of morphine-oxycodone combination may be about 12 mg/8 mg.

In some embodiments, when the net average hourly intravenous dosing is known or calculated as described above, the first dose of an immediate release morphine-oxycodone combination administered orally can be determined using the dosing algorithm shown in Table 6.

TABLE 6

Algorithm for the Conversion of Net Average Hourly Intravenous Dosing to a First Dose of an Immediate Release Morphine-Oxycodone Combination Administered Orally.

| Net Average Hourly Intravenous Dosing | First Dose of Morphine-Oxycodone Combination |
|---|---|
| 0-9 mg | 12 mg/8 mg |
| >9-≦14 mg | 18 mg/12 mg |
| >14 mg | 24 mg/16 mg |

According to the dosing algorithm of Table 6, if the net average hourly intravenous dosing is between about 0 mg and about 9 mg, the corresponding first dose of morphine-oxycodone combination may be about 12 mg/8 mg; if the net average hourly intravenous dosing is greater than about 9 mg and less than or equal to about 14 mg, the corresponding first dose of morphine-oxycodone combination may be about 18 mg/12 mg. If the net average hourly intravenous morphine administered is greater than about 14 mg, the corresponding first dose of morphine-oxycodone combination may be about 24 mg of morphine and about 16 mg of oxycodone.

After the treatment regimen is converted, the morphine-oxycodone combination may be administered to the patients every 2 to 10 hours, or every 3 to 8 hours, or every 4 to 6 hours. Alternatively, the morphine-oxycodone combination may be administered at the discretion of the physician applying the method and prescribing the combination. For opioid tolerant patients, the physician should take into consideration the patient's prior opioid dose and PCA dose of morphine and dose the subject accordingly.

After the first oral immediate release dose of the morphine-oxycodone combination, one or more subsequent doses may be administered about every four to six hours apart. In certain embodiments, the one or more subsequent doses may comprise the same amount of morphine or a pharmaceutically acceptable salt thereof and oxycodone or pharmaceutically acceptable salt thereof as the first dose. In the event the patient requires greater analgesia than what resulted from the first dose of morphine and oxycodone, the one or more subsequent doses can be increased compared to the first dose (up-titration). Thus, in certain embodiments, the subsequent doses of morphine-oxycodone combination may be co-administered about every four to six hours apart as follows:

(i) if the first dose is about 3 mg of morphine, or a pharmaceutically acceptable salt thereof, and about 2 mg of oxycodone, or a pharmaceutically acceptable salt thereof, then the first subsequent dose may be about 6 mg of morphine, or a pharmaceutically acceptable salt thereof, and about 4 mg of oxycodone, or a pharmaceutically acceptable salt thereof;

(ii) if the first dose is about 6 mg of morphine, or a pharmaceutically acceptable salt thereof, and about 4 mg of oxycodone, or a pharmaceutically acceptable salt thereof, then the first subsequent dose may be about 9 mg of morphine, or a pharmaceutically acceptable salt thereof, and about 6 mg of oxycodone, or a pharmaceutically acceptable salt thereof;

(iii) if the first dose is about 9 mg of morphine, or a pharmaceutically acceptable salt thereof, and about 6 mg of oxycodone, or a pharmaceutically acceptable salt thereof, then the first subsequent dose may be about 12 mg of morphine, or a pharmaceutically acceptable salt thereof, and about 8 mg of oxycodone, or a pharmaceutically acceptable salt thereof;

(iv) if the first dose is about 12 mg of morphine, or a pharmaceutically acceptable salt thereof, and about 8 mg of oxycodone, or a pharmaceutically acceptable salt thereof, then the first subsequent dose may be about 18 mg of morphine, or a pharmaceutically acceptable salt thereof, and about 12 mg of oxycodone, or a pharmaceutically acceptable salt thereof; and (v) if the first dose is about 18 mg of morphine, or a pharmaceutically acceptable salt thereof, and about 12 mg of oxycodone, or a pharmaceutically acceptable salt thereof, then the first subsequent dose may be about 24 mg of morphine, or a pharmaceutically acceptable salt thereof, and about 16 mg of oxycodone, or a pharmaceutically acceptable salt thereof.

In the event that the patient requires lower doses than the first administered oral immediate dose of morphine and oxycodone to maintain analgesia or because of adverse effects, the one or more subsequent doses may be decreased compared to the first dose (down-titration). Thus, in some embodiments, subsequent doses of morphine and oxycodone are co-administered about every four to six hours apart as follows:

(i) if the first dose is about 24 mg of morphine, or a pharmaceutically acceptable salt thereof, and about 16 mg of oxycodone, or a pharmaceutically acceptable salt thereof, then the first subsequent dose may be about 18 mg of morphine, or a pharmaceutically acceptable salt thereof, and about 12 mg of oxycodone, or a pharmaceutically acceptable salt thereof;

(ii) if the first dose is about 18 mg of morphine, or a pharmaceutically acceptable salt thereof, and about 12 mg of oxycodone, or a pharmaceutically acceptable salt thereof, then the first subsequent dose may be about 12 mg of morphine, or a pharmaceutically acceptable salt thereof, and about 8 mg of oxycodone, or a pharmaceutically acceptable salt thereof;

(iii) if the first dose is about 12 mg of morphine, or a pharmaceutically acceptable salt thereof, and about 8 mg of oxycodone, or a pharmaceutically acceptable salt thereof, then the first subsequent dose may be about 9 mg of morphine, or a pharmaceutically acceptable salt thereof, and about 6 mg of oxycodone, or a pharmaceutically acceptable salt thereof;

(iv) if the first dose is about 9 mg of morphine, or a pharmaceutically acceptable salt thereof, and about 6 mg of oxycodone, or a pharmaceutically acceptable salt thereof, then the first subsequent dose may be about 6 mg of morphine, or a pharmaceutically acceptable salt thereof, and about 4 mg of oxycodone, or a pharmaceutically acceptable salt thereof; and (v) if the first dose is about 6 mg of morphine, or a pharmaceutically acceptable salt thereof, and about 4 mg of oxycodone, or a pharmaceutically acceptable salt thereof, then the first subsequent dose may be about 3 mg of morphine, or a pharmaceutically acceptable salt thereof, and about 2 mg of oxycodone, or a pharmaceutically acceptable salt thereof.

Patients who no longer require analgesia may terminate the administration of the medication. However, depending on the dose that is being administered, if a patient is taking the dose on a regular basis (usually at least three to four times per day) for seven days, termination of the medication may lead to withdrawal and the symptoms may include anxiety, muscle aches, abdominal cramping, diarrhea, nausea and vomiting. A dosing algorithm to reduce or prevent withdrawal symptoms associated with termination of the morphine-oxycodone combination may be found in Table 7.

TABLE 7

Dosing Algorithm for Termination of an Administration of Morphine-Oxycodone.

| Current Combination of Oral Morphine and Oxycodone Dose | Down-Titration* |
| --- | --- |
| About 3 mg/2 mg | Can stop administration |
| About 6 mg/4 mg | Can stop administration |
| About 12 mg/8 mg | Down-titrate to about 6 mg/4 mg for about 1-2 days, then stop administration |
| About 18 mg/12 mg | Down-titrate to about 12 mg/8 mg for about 2 days, then to about 6 mg/4 mg for about 1-2 days, then stop administration |
| About 24 mg/16 mg | Down-titrate to about 12 mg/8 mg for about 2 days, then to about 6 mg/4 mg for about 1-2 days, then stop administration |

*If a patient experiences any signs or symptoms of withdrawal, then the dose should be increased to the prior dose and the down-titration should be tapered more slowly.

Morphine-Oxycodone Combination

As described above, the morphine-oxycodone combination may comprise morphine or a pharmaceutically acceptable salt thereof, and oxycodone or a pharmaceutically acceptable salt thereof. The salt may be selected from a group including, but not limited to, hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates. In some embodiments, the pharmaceutically acceptable salt of morphine may be a hydrochloride, a sulfate or a tartrate salt, and the pharmaceutically acceptable salt of oxycodone may be a hydrochloride, a terephthalate or a pectinate salt. In particular embodiments, the morphine-oxycodone combination comprises morphine sulfate and oxycodone hydrochloride.

The morphine-oxycodone combination may comprise morphine, or a pharmaceutically acceptable salt thereof, in a different pharmaceutical composition from oxycodone, or a pharmaceutically acceptable salt thereof. In particular embodiments, morphine sulfate and oxycodone hydrochloride are in the same pharmaceutical composition.

A suitable combination product of morphine and oxycodone, or pharmaceutically acceptable salts thereof, is disclosed in co-pending U.S. patent application Ser. Nos. 11/544,187, 12/469,438, and 12/567,209.

The pharmaceutical compositions for oral administration may be administered in immediate release dosage forms. Immediate release dosage forms such as solid or liquid dosage forms include, by way of example and not limitation, tablets, troches, capsules, dispersions, suspensions, solutions, syrups, and the like. Pharmaceutical compositions may be presented as discrete units such as capsules, sachets or tablets, each containing a predetermined amount of each of the morphine and oxycodone, or pharmaceutically acceptable salts thereof, as a powder or granules or as a solution or a suspension in an aqueous liquid, a non-aqueous liquid, an oil-in-water liquid emulsion or a water-in-oil liquid emulsion. Such compositions may be prepared by any of the methods of pharmacy but all methods include the step of bringing together each of the opioids with a pharmaceutically acceptable carrier. In general, the compositions may be prepared by uniformly and intimately admixing the morphine and oxycodone, or pharmaceutically acceptable salts thereof, with liquid carriers or finely divided solid carriers or both, and then, if necessary, shaping the product into the desired presentation. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents together with pharmaceutically active substances is well known in the art. These carriers include, by way of example and not limitation, sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water. Supplementary active compounds can also be incorporated into the compositions.

Oral compositions generally may include an inert diluent or an edible carrier. Suitable oral compositions may be, e.g., enclosed in gelatin capsules or compressed into tablets, troches, or capsules. For the purpose of oral therapeutic administration, the active compound may be incorporated with excipients and used in the form of tablets, troches, or capsules. Pharmaceutically compatible binding agents, and/or adjuvant materials may be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

It is especially advantageous to formulate oral compositions in dosage unit form for ease of administration and uniformity of dosage. The term "dosage unit form" as used herein refers to physically discrete units suited as unitary dosages for the patient to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions for oral administration may also be administered in controlled release dosage forms. For example, controlled release dosage forms as described hereinafter may be administered every 12- or 24-hours comprising, respectively, about 3 or 6 times the amount of the immediate-release dosage form. In this regard, it is well known that the change from immediate-release dosages to controlled-release dosages of morphine and oxycodone, or pharmaceutically acceptable salts thereof, may be a simple milligram to milligram conversion that results in the same total "around-the-clock" dose of the morphine and oxycodone, or pharmaceutically acceptable salts thereof. See Cherny and Portenoy, "*Practical Issues in the Management of Cancer Pain*," in *Textbook of Cancer Pain*, Third Edition, Eds. Wall and Meizack, Churchill Livingstone, 1994, 1453.

Controlled-release of the morphine and oxycodone, or pharmaceutically acceptable salts thereof, may be affected by incorporating the morphine and oxycodone, or pharmaceutically acceptable salts thereof, into, by way of example and not limitation, hydrophobic polymers, including acrylic resins, waxes, higher aliphatic alcohols, polylactic and polyglycolic acids and certain cellulose derivatives, such as hydroxypropylmethyl cellulose. In addition, the controlled release may be affected by using other polymer matrices, liposomes and/or microspheres. The controlled release formulation of morphine and oxycodone, or pharmaceutically acceptable salts thereof, may be released at a slower rate and over a longer period of time. For example, in some embodiments, the controlled release formulation of morphine and oxycodone, or pharmaceutically acceptable salts thereof, may release effective amounts of a mixture of morphine and oxycodone, or pharmaceutically acceptable salts thereof, over 12 hours. In other embodiments, the controlled release formulation may release effective amounts of morphine and oxycodone, or pharmaceutically acceptable salts thereof, over 4 hours or over 8 hours. In still other embodiments, the controlled release formulation may release effective amounts of morphine and oxycodone, or pharmaceutically acceptable salts thereof, over 15, 18, 24 or 30 hours.

In some embodiments of the invention, the dose of the morphine component, or a pharmaceutically acceptable salt thereof, in the pharmaceutical compositions in accordance with the present invention, or methods of the present invention, for opioid-naïve human adults through oral administration and in immediate release form may be about 3 mg or more; about 6 mg or more; about 12 mg or more; about 18 mg or more; or about 24 mg or more, every four hours. For non-opioid-naïve human adults through oral administration in immediate release form, the dose of the morphine component may be higher.

In some embodiments of the invention, the analgesic dose of the oxycodone component, or a pharmaceutically acceptable salt thereof, in the pharmaceutical compositions in accordance with the present invention, or methods of the present invention, for opioid-naïve human adults through oral administration and in immediate release form may be 2 mg or more; 4 mg or more; 8 mg or more; 12 mg or more; or 16 mg or more, every four hours. For non-opioid-naïve human adults through oral administration in immediate release form, the dose of the oxycodone component may be higher.

The concentration of morphine and oxycodone in the blood stream will depend on the amount of compound administered in the composition as well as the route of administration and the specific formulation used. For example, it is well known in the art that administration of morphine and oxycodone by IV injection typically results in a significant concentration of each compound in the blood stream almost immediately after administration (without delay), whereas formulations adapted for oral administration of morphine and oxycodone will typically achieve effective concentrations in the blood stream later than IV administration and at different concentrations depending on oral availability of the compounds. Further, the routes of administration of the compounds may further result in different inactivation and excretion rates of morphine and oxycodone when administered in a combination. Therefore, it will be apparent to one of skill in the art that the absolute and relative amounts of morphine and oxycodone, or pharmaceutically acceptable salts thereof, administered to patients via oral administration to achieve efficacy with a lower incidence of adverse side effects may differ from the amounts of drugs required for IV administration or other routes of administration. Table 8 provides pharmacokinetic data for healthy subjects that were orally co-administered a single dose of morphine and oxycodone in dosage strengths of about 3 mg/2 mg and about 12 mg/8 mg. Values for the observed maximum plasma concentration ($C_{max}$), total area under the plasma concentration-time curve ($AUC_{0-\infty}$) and the time to maximum plasma concentration ($T_{max}$) were determined.

TABLE 8

Pharmacokinetic Data for Oral Co-Administration of Morphine and Oxycodone in a Ratio of about 3:2 by Weight.*

| Analyte | Dose (mg) | $C_{max}$ (ng/mL) | $AUC_{0-\infty}$** (ng·h/mL/mg) | $T_{max}$ (h) |
|---|---|---|---|---|
| Morphine | 3 (n = 18) | 3.9 | 4.24 | 0.50 |
|  | 12 (n = 18) | 16.1 | 4.55 | 0.54 |
| Oxycodone | 2 (n = 18) | 4.9 | 9.62 | 1.0 |
|  | 8 (n = 18) | 17.8 | 9.62 | 1.0 |

*Pharmacokinetic analyses were performed using WinNonlin ® Professional, Version 5.2. Standard noncompartmental analyses were conducted for computation of metrics of exposure ($C_{max}$, AUC).
**Dose Adjusted.

Plasma levels of morphine and oxycodone each appeared to increase linearly in a dose-proportionate manner after single-dose administration of the morphine:oxycodone combination (within the 3 mg/2 mg to 12 mg/8 mg dose range). All dose-normalized, log-transformed parameters ($C_{max}$ and $AUC_{0-\infty}$) were within the 80-125% bioequivalence criteria limits, a demonstration of the dose proportionality between the 3 mg/2 mg and 12 mg/8 mg dose strengths. These data provide conclusive evidence of dose proportionality between the two dosage strengths.

Method of Treating Patients

The present invention also relates to a method for the treatment of pain in a human patient in need of analgesia by oral co-administration of an immediate release morphine-oxycodone combination in a weight ratio of about 3:2. In some embodiments such method includes the use of a dosing algorithm to determine the first oral dose of the immediate release morphine-oxycodone combination following administration of IV opioid (e.g., morphine or a pharmaceutically acceptable salt thereof) to the patient. The dosing algorithm used in these methods may be a dosing algorithm described above.

For example, if the net average hourly intravenous dosing may be known or calculated, a dosing algorithm may be applied such that if the net average hourly intravenous dosing is between about 0 mg and about 9 mg, the corresponding first dose of morphine-oxycodone combination may be about 12 mg/8 mg; if the net average hourly intravenous dosing is greater than about 9 mg and less than or equal to about 14 mg, the corresponding first dose of morphine-oxycodone combination may be about 18 mg/12 mg. If the net average hourly intravenous morphine administered is greater than about 14 mg, the corresponding first dose of morphine-oxycodone combination may be about 24 mg of morphine and about 16 mg of oxycodone.

The present invention will be understood more readily by reference to the following examples, which are provided by way of illustration and are not intended to be limiting of the invention.

EXAMPLES

Example 1

A patient undergoes surgery that is completed at 12:30 PM, whereby IV PCA morphine is started at 1:00 PM. At 7:00 AM the next morning IV PCA administration of morphine is stopped and the patient is converted to oral MOXDUO®, which is a combination of morphine sulfate and oxycodone hydrochloride in the ratio of approximately 3:2 by weight in a form for oral administration for immediate release. Therefore, from the beginning of the IV PCA morphine administration to the end is a total time of 18 hours of IV PCA morphine dosing available for the calculation of the algorithm. During the first four hours of that total time of IV PCA morphine dosing, the patient receives 9 mg of morphine. The patient receives a total amount of 129 mg of morphine during the total time of IV PCA morphine administration. Therefore, the net amount of morphine administered by IV PCA is calculated by subtracting 9 mg (the amount of IV PCA morphine administered during the first four hours of IV PCA) from the total amount of 129 mg, thereby giving a net amount of morphine administered by IV PCA of 120 mg (129 mg-9 mg). The net time of IV PCA morphine administration is calculated as the total time of 18 hours minus the first four hours, for a net time of IV PCA morphine administration of 14 hours (18 hours-4 hours). The net average hourly IV PCA morphine administration is calculated by dividing the net amount of IV PCA morphine administration (120 mg) by the net time of IV PCA morphine administration (14 hours), which in this case is 120 mg divided by 14 hours, which gives an net average hourly IV morphine dosing of about 9 mg (120 mg/14 hours). With reference to Table 4 above for a net average hourly IV morphine dosing of about 9 mg per hour, the patient is converted to a corresponding first oral dose of MOXDUO® of 12 mg of morphine sulfate and 8 mg of oxycodone hydrochloride in an immediate release dosage form.

Example 2

A patient undergoes surgery that is completed at 2:00 PM, whereby IV PCA morphine is started at 2:30 PM. At 7:30 AM the next morning IV PCA administration of morphine is stopped and the patient is converted to oral MOXDUO®, which is a combination of morphine sulfate and oxycodone hydrochloride in the ratio of approximately 3:2 by weight in a form for immediate release. Therefore, from the beginning of the IV PCA morphine administration to the end is a total time of 17 hours of IV PCA morphine dosing available for the calculation of the algorithm. During the first four hours of that total time of IV PCA morphine dosing, the patient receives 9 mg of morphine IV PCA and a nurse gives 2 mg IV morphine through the PCA pump for a total of 11 mg of IV morphine during the first four hours. The patient receives a total amount of 60 mg of morphine during the total time of IV PCA morphine administration. Therefore, the net amount of morphine administered by IV PCA is calculated by subtracting from the total amount of 60 mg the amount of IV PCA morphine administered during the first four hours of IV PCA, which is 11 mg, thereby giving a net amount of morphine administered IV PCA of 49 mg (60 mg-11 mg). The net time of IV PCA morphine administration is calculated as the total time of 17 hours minus the first four hours, for a net time of IV PCA morphine administration of 13 hours (17 hours-4 hours). The net average hourly IV PCA morphine administration is calculated by dividing the net amount of IV PCA morphine administration (49 mg) by the net time of IV PCA morphine administration (11 hours), which in this case gives an net average hourly intravenous morphine dosing of about 4.5 mg (49 mg/11 hours). With reference to Table 6 above for a net average hourly intravenous morphine dosing of about 4.5 mg, the patient is therefore converted to a first dose of oral MOXDUO® at a dose of 12 mg of morphine sulfate and 8 mg of oxycodone hydrochloride in immediate release form.

Example 3

An open-label, multicenter, multiple-dose pilot study of flexible doses of oral MOXDUO® in a 3:2 ratio of morphine sulfate to oxycodone hydrochloride, compared to PERCO- CET® (1-2 tablets of 5 mg/325 mg oxycodone/acetaminophen) for the management of acute, moderate to severe postoperative pain following unilateral total knee arthroplasty or total hip arthroplasty was conducted. One objective of the study was to evaluate the adequacy of an algorithm for conversion of IV PCA morphine to oral morphine-equivalent doses of MOXDUO® administered every 4 to 6 hours over a 48-hour treatment period. Any adverse events, including Treatment-Emergent Adverse Events (TEAE) or Serious Adverse Events (SAE), including signs of abuse potential were also assessed.

Testing Protocol

Immediate post-operative analgesia consisted of PCA IV morphine. Subjects were connected to a PCA pump within 120 minutes after closure of surgery. Morphine doses (0.5-2.0 mg/dose) were administered by PCA pump with a 5-minute lockout period and a maximum dose of 10 mg morphine per hour. If the analgesia was insufficient, the one-hour limit may be increased to ~15 mg morphine per hour at the discretion of the doctor. During the course of IV PCA morphine, including prior to the initial dose of self-administered IV PCA morphine, the nursing staff may administer via the PCA pump a single bolus dose of up to 5 mg of morphine, if necessary.

Eligibility for enrollment of subjects in the study required the administration of an average oral morphine equivalent dose of <120 mg IV morphine by PCA pump (including morphine administered as a bolus by nursing staff and all self-administered morphine) over a period of at least 8 hours (interval between first dose and final dose via pump). Following surgery, subjects were disconnected from the PCA pump between 5:00 AM-7:00 AM on the morning following surgery to obtain an IV morphine baseline to be used with an algorithm to determine the starting dose for administration of oral MOXDUO®.

Calculation of total dose of morphine (mg) used during the total period of IV morphine PCA includes the sum of any morphine administered as a bolus by nursing staff and all self-administered morphine. MOXDUO® study medication was administered q. 4-6 h (not to exceed 6 doses in 24 hours) and the last dose was administered 42 hours after the first dose.

The primary efficacy endpoint was the mean Sum of Pain Intensity Difference scores during the 48-hour treatment period ($SPID_{48}$). A subject who had at least 30% decrease in pain intensity compared to baseline or had a good to excellent outcome on a global assessment of study medication scale at 24 or 48 hours was considered a responder. All adverse events were described by onset, duration, resolution, relationship, and intensity (mild, moderate, severe). The algorithm for conversion of IV morphine PCA to oral MOXDUO® is shown above in Table 3. The doses administered to the subjects throughout the study are provided below in Table 9.

TABLE 9

MOXDUO ® Doses Administered to Subjects Following IV PCA Morphine.

| Patient | Calculate 4-h Ave Oral ME[1] (mg/hr) | First Dose (mg:mg) | First Subsequent Dose (mg:mg) | Other Subsequent Doses (mg:mg) | Final Dose (mg:mg) |
|---|---|---|---|---|---|
| 1 | 21 | 12:8 | 18:12 | 18:12 | 18:12 |
| 2 | 21 | 12:8 | 18:12 | 24:16 18:12 | 18:12 |
| 3 | 9 | 12:8 | 6:4 | 6:4 | 6:4 |
| 4 | 31 | 18:12 | No change | 24:16 | 24:16 |
| 5 | 13 | 12:8 | No change | No change | 12:8 |
| 6 | 4 | 12:8 | No change | No change | 12:8 |
| 7 | 26 | 12:8 | No change | 18:12 | 18:12 |
| 8 | 11 | 12:8 | 18:12 | 12:8 | 12:8 |
| 9 | 3 | 12:8 | No change | No change | 12:8 |
| 10 | 29 | 12:8 | No change | No change | 12:8 |
| 11 | 24 | 12:8 | 18:12 | 24:16 18:12 | NA[2] |
| 12 | 27 | 12:8 | 18:12 | 24:16 | 24:16 |
| 13 | 13 | 12:8 | 18:12 | 24:16 18:12 12:8 18:12 24:16 | 24:16 |
| 14 | 7 | 12:8 | No change | No change | 12:8 |

[1]ME = morphine equivalents
[2]Subject inadvertently administered PERCOCET ® instead of MOXDUO ® at 5th dose.

The second dose (first subsequent dose) of MOXDUO® received by the subjects (4-6 hours after the first dose) was more indicative of the amount of analgesia required as the subjects became mobile and typically experienced more pain. Of the 14 subjects, 8 subjects did not require an upward dose titration for the second dose. In fact, 1 of the 14 subjects down-titrated at the first subsequent dose and completed the study at the lower dose level. During the remainder of the 48-hour study period, 6 subjects required an increased dose and completed the study at the higher dose level compared to the first administered dose.

Efficacy Results

Both MOXDUO® and PERCOCET® treatment groups had a similar proportion of responders (77% and 79%, respectively). The efficacy endpoint of the $SPID_{48}$ did not show a significant difference in values between MOXDUO® (148 points) and PERCOCET® (140 points); however, the power to detect statistical significant differences between treatments was low with these sample sizes. Nonetheless, scores on individual domains of the Brief Pain Inventory-Short Form (BPI-SF) showed a significantly greater improvement of BPI-SF scores for MOXDUO® for pain interfering with general activity than the PERCOCET® treatment group at 48 hours/early termination.

Safety Results

The dosing algorithm for converting IV PCA morphine to the first dose of oral MOXDUO® was both conservative and safe. None of the subjects administered MOXDUO® discontinued due to an adverse event, although one subject in the PERCOCET® treatment group discontinued because of a possibly related TEAE of stomach irritation. The overall incidence of nausea, pruritus, constipation, and dizziness was higher during the IV PCA morphine use than during the same time period after first dose of study medication. Eleven (25%) subjects had moderate or severe nausea while on IV PCA morphine. No moderate-severe vomiting, nausea, or dizziness was reported by subjects in the MOXDUO® treatment group, although in the PERCOCET® treatment group, moderate to severe nausea and vomiting were experienced by 4 (27%) and 3 (20%) of subjects, respectively. Ondansetron was administered during the study treatment to 6 subjects in both the MOXDUO® and PERCOCET® treatment groups. "Woozy" was the only potential abuse liability symptom that was reported and occurred in one subject in the PERCOCET® treatment group.

Conclusion

The analgesic efficacy of MOXDUO® and PERCOCET® treatment groups were similar in terms of proportion of responders and median SPID$_{48}$. In addition, values for the Sum of Pain Response and Pain Intensity Difference (SPRID), mean distance walked on Day 2 of rehabilitation, and time to remediation were similar for both treatment groups (data not shown). The MOXDUO® dosing treatment group had a significantly lower BPI-SF score for pain interfering with general activity than the PERCOCET® treatment group at 48 hours/early termination. For example, patients being administered MOXDUO® had a mean % improvement in BPI from baseline to end of treatment for general activity, walking ability, and ability to sleep of 54%, 35%, and 31%, respectively. Patients that were administered PERCOCET® had BPI scores of 19%, 17%, and 15%, respectively, for the same categories. No related SAEs, severe TEAEs, or AEs leading to discontinuation occurred in the MOXDUO® treatment group. In the PERCOCET® treatment group, 1 subject had a severe TEAE of dry mouth, and 1 subject discontinued due to an adverse event of stomach irritation. The incidence of moderate to severe nausea and vomiting was higher in the PERCOCET® treatment group compared with the equi-analgesic MOXDUO® dosing treatment group, which had no such events.

The dosing algorithms of the instant invention allows for the determination of a simple and convenient starting dose of MOXDUO® for patients being administered IV opioids, such as morphine. The titration algorithms also allow for the ease of upward and downward titration of MOXDUO®, if required. The algorithms used in the present invention provide surprising and unexpected results since patients being administered MOXDUO® reached a level of analgesia within the first administered dose, or the first subsequent dose of MOXDUO®. These results are in contrast to patients that may require up to 48-hours of dose titrations to obtain analgesia. See S. Mercadante, *Eur. J. Pain* 11 (2007) 823-30 ("In conclusion dose titration with oral opioids, particularly with short-onset drugs such as morphine, may provide adequate pain relief in about 48 hr in most patients").

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A method of converting a treatment for pain consisting essentially of intravenous administration of an opioid to a treatment for pain consisting essentially of oral co-administration of immediate release morphine sulfate and oxycodone hydrochloride in a weight ratio of about 3:2, in a human patient in need of analgesia, the method comprising:
   determining a four-hour average oral morphine equivalent dose of the opioid administered intravenously to the human patient; and
   orally co-administering to the human patient a first dose of an immediate release dosage form of morphine sulfate and oxycodone hydrochloride, wherein:
      (i) if the four-hour average oral morphine equivalent dose is between about 0 mg and about 30 mg, then the first dose is no greater than about 12 mg of morphine sulfate and about 8 mg of oxycodone hydrochloride;
      (ii) if the four-hour average oral morphine equivalent dose is greater than about 30 mg and less than or equal to about 40 mg, then the first dose is about 18 mg of morphine sulfate and about 12 mg of oxycodone hydrochloride;
      (iii) if the four-hour average oral morphine equivalent dose is greater than about 40 mg and less than or equal to about 120 mg, then the first dose is about 24 mg of morphine sulfate and about 16 mg of oxycodone hydrochloride;
   wherein the opioid is morphine or oxycodone, or a pharmaceutically acceptable salt thereof.

2. The method of claim 1, wherein:
   a. if the four-hour average oral morphine equivalent dose is between about 0 mg and about 10 mg, then the first dose is about 3 mg of morphine sulfate and about 2 mg of oxycodone hydrochloride;
   b. if the four-hour average oral morphine equivalent dose is greater than about 10 mg and less than or equal to about 15 mg, then the first dose is about 6 mg of morphine sulfate and about 4 mg of oxycodone hydrochloride;
   c. if the four-hour average oral morphine equivalent dose is greater than about 15 mg and less than or equal to about 20 mg, then the first dose is about 9 mg of morphine sulfate and about 6 mg of oxycodone hydrochloride;
   d. if the four-hour average oral morphine equivalent dose is greater than about 20 mg and less than or equal to about 30 mg, then the first dose is about 12 mg of morphine sulfate and about 8 mg of oxycodone hydrochloride.

3. The method of claim 1, wherein if the four-hour average oral morphine equivalent dose is between about 0 mg and about 30 mg, then the first dose is about 12 mg of morphine sulfate and about 8 mg of oxycodone hydrochloride.

4. The method of claim 1, wherein morphine sulfate and oxycodone hydrochloride are co-administered in a single dosage form.

5. The method of claim 1, wherein the four-hour average oral morphine equivalent dose is determined according to equation 1:

$$\begin{pmatrix} \text{4-Hour Average} \\ \text{Oral Morphine} \\ \text{Equivalent Dose} \end{pmatrix} = \left( \frac{m-n}{h-4} \times 4 \right) \times b \times s \qquad (1)$$

wherein m is the amount (mg) of the opioid administered intravenously, n is the amount (mg) of opioid administered during the first four hours of intravenous administration, h is the total hours of opioid intravenous administration, b is a clinical bioequivalency factor, and s is a safety factor.

6. The method of claim 5, wherein the clinical bioequivalency factor is about 2.

7. The method of claim 5, wherein the safety factor is about 0.75.

8. The method of claim 1, comprising orally co-administering one or more subsequent doses of morphine sulfate and oxycodone hydrochloride about every four to six hours, wherein the one or more subsequent doses comprises the same amount of morphine sulfate and oxycodone hydrochloride as the first dose.

9. The method of claim 1, comprising orally co-administering one or more subsequent doses of morphine sulfate and oxycodone hydrochloride about every four to six hours, wherein:
   (i) if the first dose is about 12 mg of morphine sulfate and about 8 mg of oxycodone hydrochloride, then the first subsequent dose is about 18 mg of morphine sulfate and about 12 mg of oxycodone hydrochloride;
   (ii) if the first dose is about 18 mg of morphine sulfate and about 12 mg of oxycodone hydrochloride, then the first subsequent dose is about 24 mg of morphine sulfate and about 16 mg of oxycodone hydrochloride.

10. The method of claim 2, comprising orally co-administering one or more subsequent doses of morphine sulfate and oxycodone hydrochloride about every four to six hours, wherein:
   a. if the first dose is about 3 mg of morphine sulfate and about 2 mg of oxycodone hydrochloride, then the first subsequent dose is about 6 mg of morphine sulfate and about 4 mg of oxycodone hydrochloride;
   b. if the first dose is about 6 mg of morphine sulfate and about 4 mg of oxycodone hydrochloride, then the first subsequent dose is about 9 mg of morphine sulfate and about 6 mg of oxycodone hydrochloride;
   c. if the first dose is about 9 mg of morphine sulfate and about 6 mg of oxycodone hydrochloride, then the first subsequent dose is about 12 mg of morphine sulfate and about 8 mg of oxycodone hydrochloride;
   d. if the first dose is about 12 mg of morphine sulfate and about 8 mg of oxycodone hydrochloride, then the first subsequent dose is about 18 mg of morphine sulfate and about 12 mg of oxycodone hydrochloride;
   e. if the first dose is about 18 mg of morphine sulfate and about 12 mg of oxycodone hydrochloride, then the first subsequent dose is about 24 mg of morphine sulfate and about 16 mg of oxycodone hydrochloride.

11. The method of claim 1, comprising orally co-administering one or more subsequent doses of morphine sulfate and oxycodone hydrochloride about every four to six hours, wherein:
   (i) if the first dose is about 24 mg of morphine sulfate and about 16 mg of oxycodone hydrochloride, then the first subsequent dose is about 18 mg of morphine sulfate and about 12 mg of oxycodone hydrochloride;
   (ii) if the first dose is about 18 mg of morphine sulfate and about 12 mg of oxycodone hydrochloride, then the first subsequent dose is about 12 mg of morphine sulfate and about 8 mg of oxycodone hydrochloride;
   (iii) if the first dose is about 12 mg of morphine sulfate and about 8 mg of oxycodone hydrochloride, then the first subsequent dose is about 9 mg of morphine sulfate and about 6 mg of oxycodone hydrochloride.

12. The method of claim 2, comprising orally co-administering one or more subsequent doses of morphine sulfate and oxycodone hydrochloride about every four to six hours, wherein:
   (i) if the first dose is about 24 mg of morphine sulfate and about 16 mg of oxycodone hydrochloride, then the first subsequent dose is about 18 mg of morphine sulfate and about 12 mg of oxycodone hydrochloride;
   (ii) if the first dose is about 18 mg of morphine sulfate and about 12 mg of oxycodone hydrochloride, then the first subsequent dose is about 12 mg of morphine sulfate and about 8 mg of oxycodone hydrochloride;
   (iii) if the first dose is about 12 mg of morphine sulfate and about 8 mg of oxycodone hydrochloride, then the first subsequent dose is about 9 mg of morphine sulfate and about 6 mg of oxycodone hydrochloride;
   (iv) if the first dose is about 9 mg of morphine sulfate and about 6 mg of oxycodone hydrochloride, then the first subsequent dose is about 6 mg of morphine sulfate and about 4 mg of oxycodone hydrochloride;
   (v) if the first dose is about 6 mg of morphine sulfate and about 4 mg of oxycodone hydrochloride, then the first subsequent dose is about 3 mg of morphine sulfate and about 2 mg of oxycodone hydrochloride.

13. A method of converting a treatment for pain consisting essentially of intravenous administration of morphine to a treatment for pain consisting essentially of oral co-administration of immediate release morphine sulfate and oxycodone hydrochloride in a weight ratio of about 3:2, in a human patient in need of analgesia, the method comprising:
   determining a four-hour average oral morphine equivalent dose of morphine administered intravenously to the human patient; and
   orally co-administering to the human patient a first dose of an immediate release dosage form of morphine sulfate and oxycodone hydrochloride, wherein:
   (i) if the four-hour average oral morphine equivalent dose is between about 0 mg and about 30 mg, then the first dose is no greater than about 12 mg of morphine sulfate and about 8 mg of oxycodone hydrochloride;
   (ii) if the four-hour average oral morphine equivalent dose is greater than about 30 mg and less than or equal to about 40 mg, then the first dose is about 18 mg of morphine sulfate and about 12 mg of oxycodone hydrochloride;
   (iii) if the four-hour average oral morphine equivalent dose is greater than about 40 mg and less than or equal to about 120 mg, then the first dose is about 24 mg of morphine sulfate and about 16 mg of oxycodone hydrochloride.

14. The method of claim 13, wherein:
   a. if the four-hour average oral morphine equivalent dose is between about 0 mg and about 10 mg, then the first dose is about 3 mg of morphine sulfate and about 2 mg of oxycodone hydrochloride;
   b. if the four-hour average oral morphine equivalent dose is greater than about 10 mg and less than or equal to about 15 mg, then the first dose is about 6 mg of morphine sulfate and about 4 mg of oxycodone hydrochloride;
   c. if the four-hour average oral morphine equivalent dose is greater than about 15 mg and less than or equal to about 20 mg, then the first dose is about 9 mg of morphine sulfate and about 6 mg of oxycodone hydrochloride;
   d. if the four-hour average oral morphine equivalent dose is greater than about 20 mg and less than or equal to about 30 mg, then the first dose is about 12 mg of morphine sulfate and about 8 mg of oxycodone hydrochloride.

15. The method of claim 13, wherein if the four-hour average oral morphine equivalent dose is between about 0 mg and about 30 mg, then the first dose is about 12 mg of morphine sulfate and about 8 mg of oxycodone hydrochloride.

16. The method of claim 13, comprising orally co-administering one or more subsequent doses of morphine sulfate and oxycodone hydrochloride about every four to six hours, wherein:
   (i) if the first dose is about 12 mg of morphine sulfate and about 8 mg of oxycodone hydrochloride, then the first subsequent dose is about 18 mg of morphine sulfate and about 12 mg of oxycodone hydrochloride;
   (ii) if the first dose is about 18 mg of morphine sulfate and about 12 mg of oxycodone hydrochloride, then the first subsequent dose is about 24 mg of morphine sulfate and about 16 mg of oxycodone hydrochloride.

17. The method of claim 14, comprising orally co-administering one or more subsequent doses of morphine sulfate and oxycodone hydrochloride about every four to six hours, wherein:
   a. if the first dose is about 3 mg of morphine sulfate and about 2 mg of oxycodone hydrochloride, then the first subsequent dose is about 6 mg of morphine sulfate and about 4 mg of oxycodone hydrochloride;

b. if the first dose is about 6 mg of morphine sulfate and about 4 mg of oxycodone hydrochloride, then the first subsequent dose is about 9 mg of morphine sulfate and about 6 mg of oxycodone hydrochloride;
c. if the first dose is about 9 mg of morphine sulfate and about 6 mg of oxycodone hydrochloride, then the first subsequent dose is about 12 mg of morphine sulfate and about 8 mg of oxycodone hydrochloride;
d. if the first dose is about 12 mg of morphine sulfate and about 8 mg of oxycodone hydrochloride, then the first subsequent dose is about 18 mg of morphine sulfate and about 12 mg of oxycodone hydrochloride;
e. if the first dose is about 18 mg of morphine sulfate and about 12 mg of oxycodone hydrochloride, then the first subsequent dose is about 24 mg of morphine sulfate and about 16 mg of oxycodone hydrochloride.

18. The method of claim 13, comprising orally co-administering one or more subsequent doses of morphine sulfate and oxycodone hydrochloride about every four to six hours, wherein:
   (i) if the first dose is about 24 mg of morphine sulfate and about 16 mg of oxycodone hydrochloride, then the first subsequent dose is about 18 mg of morphine sulfate and about 12 mg of oxycodone hydrochloride;
   (ii) if the first dose is about 18 mg of morphine sulfate and about 12 mg of oxycodone hydrochloride, then the first subsequent dose is about 12 mg of morphine sulfate and about 8 mg of oxycodone hydrochloride;
   (iii) if the first dose is about 12 mg of morphine sulfate and about 8 mg of oxycodone hydrochloride, then the first subsequent dose is about 9 mg of morphine sulfate and about 6 mg of oxycodone hydrochloride.

19. The method of claim 14, comprising orally co-administering one or more subsequent doses of morphine sulfate and oxycodone hydrochloride about every four to six hours, wherein:
   (i) if the first dose is about 24 mg of morphine sulfate and about 16 mg of oxycodone hydrochloride, then the first subsequent dose is about 18 mg of morphine sulfate and about 12 mg of oxycodone hydrochloride;
   (ii) if the first dose is about 18 mg of morphine sulfate and about 12 mg of oxycodone hydrochloride, then the first subsequent dose is about 12 mg of morphine sulfate and about 8 mg of oxycodone hydrochloride;
   (iii) if the first dose is about 12 mg of morphine sulfate and about 8 mg of oxycodone hydrochloride, then the first subsequent dose is about 9 mg of morphine sulfate and about 6 mg of oxycodone hydrochloride;
   (iv) if the first dose is about 9 mg of morphine sulfate and about 6 mg of oxycodone hydrochloride, then the first subsequent dose is about 6 mg of morphine sulfate and about 4 mg of oxycodone hydrochloride;
   (v) if the first dose is about 6 mg of morphine sulfate and about 4 mg of oxycodone hydrochloride, then the first subsequent dose is about 3 mg of morphine sulfate and about 2 mg of oxycodone hydrochloride.

20. A method of converting a treatment for pain consisting essentially of intravenous administration of morphine to a treatment for pain consisting essentially of oral co-administration of immediate release morphine sulfate and oxycodone hydrochloride in a weight ratio of about 3:2, in a human patient in need of analgesia, the method comprising:
   determining a four-hour average oral morphine equivalent dose of morphine administered intravenously to the human patient; and
   orally co-administering to the human patient a first dose of an immediate release dosage form of morphine sulfate and oxycodone hydrochloride, wherein:
      (i) if the four-hour average oral morphine equivalent dose is between about 0 mg and about 30 mg, then the first dose is about 12 mg of morphine sulfate and about 8 mg of oxycodone hydrochloride;
      (ii) if the four-hour average oral morphine equivalent dose is greater than about 30 mg and less than or equal to about 40 mg, then the first dose is about 18 mg of morphine sulfate and about 12 mg of oxycodone hydrochloride;
      (iii) if the four-hour average oral morphine equivalent dose is greater than about 40 mg and less than or equal to about 120 mg, then the first dose is about 24 mg of morphine sulfate and about 16 mg of oxycodone hydrochloride.

* * * * *